United States Patent [19]

Giani et al.

[11] Patent Number: 4,971,980
[45] Date of Patent: Nov. 20, 1990

[54] PHARMACOLOGICALLY ACTIVE BENZIMIDAZOLE DERIVATIVES

[75] Inventors: Roberto P. Giani; Ettore Parini; Giancarlo Tonon, all of Milan, Italy

[73] Assignee: Dompe Farmaceutici S.p.A., Milan, Italy

[21] Appl. No.: 376,075

[22] Filed: Jul. 6, 1989

[30] Foreign Application Priority Data

Jul. 7, 1988 [IT] Italy ................. 21271 A/88

[51] Int. Cl.$^5$ ................. C07D 211/10; C07D 235/14; A61K 31/415; A61K 31/445
[52] U.S. Cl. ..................... 514/322; 546/199; 548/330; 548/327; 514/394
[58] Field of Search ............... 548/330, 327; 546/199; 514/322, 394

[56] References Cited

PUBLICATIONS

*Chemical Abstracts*, 65:15365e(1966)[C. Ganellin et al.,*J. Heterocyclic Chem.* 3(3), 278-281(1966)].

*Primary Examiner*—Mary C. Lee
*Assistant Examiner*—Jacqueline Haley
*Attorney, Agent, or Firm*—Armstrong, Nikaido, Marmelstein, Kubovcik & Murray

[57] ABSTRACT

Novel benzimidazole derivatives (I) are described, of formula

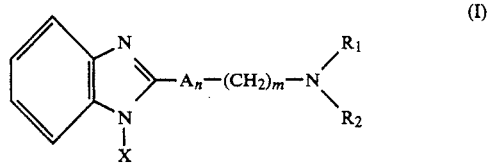

wherein
A represents

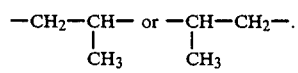

n is 0 or 1;
m represents 0 or an integer of from 1 to 5 inclusive, provided that when n is 0, m represents an integer of from 2 to 5 inclusive;
X represents a radical selected from the group consisting of benzyl, fluorobenzyl, alkoxyalkyl and tetrahydrofurfuryl;
$R_1$ and $R_2$ represent each a saturated or unsaturated alkyl radical having of from 1 to 4 carbon atoms or they may form, together with the adjacent nitrogen atom, an optionally substituted heterocyclic ring selected from the group consisting of pyrrolidine and piperidine, and the corresponding, non-toxic, pharmaceutically acceptable acid addition salts.

The compounds (I) are endowed with an interesting antihistaminic activity.

6 Claims, No Drawings

PHARMACOLOGICALLY ACTIVE BENZIMIDAZOLE DERIVATIVES

The present invention relates to novel benzimidazole derivatives which belong to the class having the structure formula:

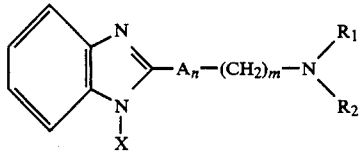

wherein

A represents

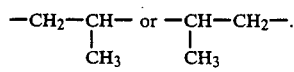

n is 0 or 1;

m represents 0 or an integer of from 1 to 5 inclusive, provided that when n is 0, m represents an integer of from 2 to 5 inclusive;

X represents a radical selected from the group consisting of benzyl, fluorobenzyl, alkoxyalkyl and tetrahydrofurfuryl;

$R_1$ and $R_2$ represent each a saturated or unsaturated alkyl radical having of from 1 to 4 carbon atoms or they may form, together with the adjacent nitrogen atom, an optionally substituted heterocyclic ring; more particularly they may represent an optionally substituted heterocyclic ring selected from the group consisting of pyrrolidine and piperidine, and the corresponding, non-toxic, pharmaceutically acceptable acid addition salts.

The compounds of formula (I) can be easily obtained starting from o-phenylendiamine which is reacted in warm conditions with a suitable acid HOOC—A$_n$—(CH$_2$)$_m$—N(R$_1$)R$_2$, wherein A,n,m,R$_1$ and R$_2$ have the above-mentioned meanings, then treating the so obtained benzimidazole (II), in an alkaline ambient in the presence of a suitable organic solvent, with a suitable halide HalX wherein Hal is preferably a chlorine or bromine atom and X has the above-mentioned meaning.

This process may be schematically represented as follows:

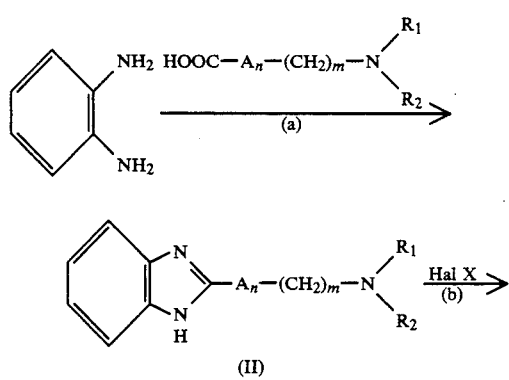

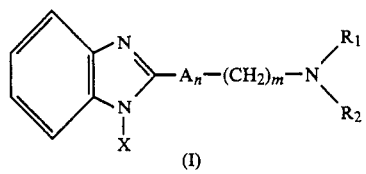

The reaction (a) is carried out at a high temperature, generally at a temperature between 130° and 190° C., while reaction (b) is performed at a lower temperature, generally at a temperature between 30° and 70° C., in a suitable aprotic solvent, preferably N,N-dimethylformamide, and in the presence of sodium hydride.

Both the intermediate products (II) and the end products (I) may be usefully isolated as non-toxic, suitable, pharmaceutically acceptable acid addition salts, such as, e.g., those obtained with fumaric, maleic and succinic acid.

The compounds (I) have demonstrated to possess an interesting antihistaminic activity which is particularly displayed by oral route.

The anti-histaminic activity of the compounds of the invention has been evaluated studying either the effect on the mortality induced by histamine, the affinity towards $H_1$ histaminergic receptors and the effect on the sleeping time interval induced by sodium pentobarbital. The tests were carried out according the following methods.

Effect on the Mortality Induced by Histamine

The method described by Romer D. et al. (Med.Welt, 17, 791, 1966) was followed and the tests were carried out on male albino guinea pigs (Dunkin-Hartley), weighing 350–450 g, which were kept in cages with a grid floor, on an empty stomach for 24 hrs with water ad libitum.

The compounds under examination were dissolved in 0,5% carboxymethylcellolose and orally administered to the animals; 60 minutes later the same animals were intravenously treated with 1,25 mg/kg of histamine dihydrochloride in saline solution. The control animals, to which only the histamine solution had been administered, showed a 100% mortality.

It was evaluated $ED_{50}$ which corresponds to the amount of the compound able to inhibit 50% of the mortality induced by histamine: the estimation of $ED_{50}$ was carried out applying the 'probit' method (Finney D. J., Statistical methods in biological assay, pg 512, 1957).

Evaluation of the Affinity Towards $H_1$ Histaminergic Receptors

The affinity of the examined compounds towards $H_1$ histaminergic receptors was evaluated by displacement curves which were obtained at different concentrations, against [$^3$H]Mepyramine in homogenates of rat brain 'in toto' according to the method described by Traub et al. (Proc.Natl.Acad.Sci.,75, 6290, 1978) with minor modifications.

The incubation was performed at 25° C. for 15 minutes, in a final volume of 1 ml of 50 mM Na/K phosphate buffer, pH 7.5, in the presence of 2 mM[$^3$H]Mepyramine and 1.5 mg of cerebral protein.

The test compounds were dissolved in phosphate buffer or dimethylsulfoxide (DMSO), the final concentration of DMSO was 0.5%. Incubation was terminated by filtration through glass fiber GF/B filters pre-soaked with 0.1% polyethylenimine (PEI); the radioactivity trapped by filters was counted by liquid scintillation.

Effect on the Sleeping Time Interval Induced by Pentobarbital

The tests were carried out on male mice Swiss-Nos (Nossan, Correzzana, Milano) weighing 20–24 g, on an empty stomach for 18 hrs, according to the method described by Turner (Screening Methods in Pharmacology, Acad. Press, pg 70,1965). The sleep was induced by intraperitoneal administration of 40 mg/kg sodium pentobarbital. The narcosis start was considered from the moment when the animal, lying on its back, lost its straightening reflex. The narcosis end was considered from the moment when the animal recovered such reflex.

The carrier or the compounds under examination were intraperitoneally administered 30 minutes before the pentobarbital administration.

The resulting data are expressed as sleeping time increase per cent of the treated animals in comparison with the controls.

It was evaluated $ED_{100}$ which represents the concentration of the examined compound necessary to double the sleeping time in comparison to that showed by the control group.

The Letal Dose$_{50}$ ($LD_{50}$) was evaluated on mice using Swiss-Nos (Nossan, Correzzana, Milano) mice weighing 18–20 g each. The animals, divided into groups of 10 animals each (5M +5F), were on an empty stomach for 18 hrs, with water ad libitum, and kept in cages with grid floor. The compounds (I) were dissolved in water or suspended in 0.5% carboxymethylcellulose and intraperitoneally administered to the animals (10 ml/kg). The mortality occured in the tested animals within the following 6 hours was noted down. At the expiry of the 6th hour, the animals were allowed to eat up to the end of the experimentation which lasted 14 days. During this period all the toxic symptoms and the mortality occuring were noted.

The animals which died during the test period and those which were sacrificed at the end of the same, underwent autopsy for a macroscopic examination of their main organs. The experimental data were statistically compared with the $X^2$ method and $LD_{50}$ was extrapolated by the 'probit' method.

The data resulting from the tests carried out on some significant compounds of the class (I), evaluated in comparison to the well known antihistaminic compound Terfenadine, are given in the following Table.

TABLE

| Compound | Histamine mortality $ED_{50}$ ug/ kg os | H-receptor 1 binding Ki (nM) | sleeping time % increase $ED_{100}$ mg/ kg i.p. | Acute toxicity $LD_{50}$ mg/ kg i.p. |
|---|---|---|---|---|
| Example 1 | 4.54 (2.47–8.36) | 5.8 | IN | 250 |
| Example 6 | 26.0 (7.0–98.1) | 6.1 | IN | >100 |
| Example 9 | 5.01 (3.10–8.12) | 6.1 | IN | >100 |
| Terfenadine | 179.00 (49–652) | 283.2 | 42 (37–50) | >100 |

IN = inactive at the dose of 100 mg/kg i.p.

For therapeutic administration, the compounds according to the present invention are used in the form of pharmaceutical preparation which contain said compounds in admixture with pharmaceutically acceptable carriers such as an organic or inorganic solid or liquid excipient suitable for oral or parenteral administration. The compounds of the invention may be contained in these pharmaceutical preparations in the form of free base or in the form of their non-toxic acid addition salts. The inorganic acids which may be employed to prepare these acid addition salts may be, e.g., hydrochloric or sulphuric acid. The organic acids which may be employed are, e.g., maleic, fumaric and succinic acid.

The pharmaceutical preparations may be in solid form as capsules, tablets, dragees or in liquid form such as solutions, suspensions or emulsions. If desired, there may be included in the above preparations auxiliary substances such as stabilizing agent and other commonly used additives, or there may be contained other therapeutically active agents suitable to be administered together with the compounds of the invention. The dosage of the compounds will vary from the administration route and will also depend upon the age and condition of the patient.

The following Examples are given by way of better illustrating the invention, but without limiting it.

EXAMPLE 1

1-(2-Ethoxyethyl)-2-(3-dimethylaminopropyl)benzimidazole

Grams 10 4-dimethylaminobutyric acid hydrochloride are heated up till melting together with 6.45 g o-phenylendiamine then it is allowed to cool and 150 ml water are added thereto. The solution is washed with dichloromethane, made alkaline and extracted with dichloromethane. The extracts are collected together, filtered on charcoal, made anhydrous on sodium sulphate and evaporated to dryness. A thick oily reddish residue is obtained, which is triturated with 200 ml diethyl ether to give 5.8 g 2-(3-dimethylaminopropyl)-benzimidazole melting at 117°–119° C.

Grams 6 2-(3-dimethylaminopropyl)benzimidazole in 100 ml N,N-dimethylformamide are treated with 1.8 g 60% sodium hydride, the mixture is warmed up to 60° C. and 4 g 2-ethoxyethyl chloride are added thereto. It is maintained at 60° C. for 5 hours, then it is poured into water, extracted with diethyl ether and the extracts washed thoroughly with water, filtered on charcoal, made anhydrous on sodium sulphate and evaporated to dryness. The residue is chromatographied on silica gel column eluting with chloroform:methyl alcohol (9:1) and it gives 1-(2-ethoxyethyl)-2-(3-dimethylaminopropyl)benzimidazole.

| Elementary analysis for $C_{16}H_{25}N_3O$ | | | |
|---|---|---|---|
| | C | H | N |
| calculated % | 69.78 | 9.15 | 15.26 |
| found % | 70.11 | 9.30 | 15.00 |

EXAMPLES 2–13

Operation was carried out according to the above described method and the following compounds were prepared.

EX. 2

1-(2-Ethoxyethyl)-2-(5-dimethylaminovaleryl)benzimidazole, starting from 2-(5-dimethylaminovaleryl)- benzimidazole (mp. 117°–119° C.) and 2-ethoxyethyl chloride.

Elementary analysis for $C_{18}H_{29}N_3O$

|  | C | H | N |
|---|---|---|---|
| calculated % | 71.25 | 9.63 | 13.85 |
| found % | 69.93 | 9.74 | 13.72 |

EX. 3

1-(2-Ethoxyethyl)-2-(3-piperidin-1-ylpropyl)benzimidazole as an oil, starting from 2-(3-piperidin-1-ylpropyl)benzimidazole (mp. 97°–102° C.) and 2-ethoxyethyl chloride.

Elementary analysis for $C_{19}H_{29}N_3O$

|  | C | H | N |
|---|---|---|---|
| calculated % | 72.34 | 9.27 | 13.32 |
| found % | 72.47 | 9.35 | 13.21 |

EX. 4

1-(2-Ethoxyethyl)-2-(4-piperidin-1-ylbutyl)benzimidazole as an oil, starting from 2-(4-piperidin-1-ylbutyl)benzimidazole (mp.146°–148° C.) and 2-ethoxyethyl chloride.

Elementary analysis for $C_{20}H_{31}N_3O$

|  | C | H | N |
|---|---|---|---|
| calculated % | 72.91 | 9.48 | 12.75 |
| found % | 73.12 | 9.54 | 12.68 |

EX. 5

1-Benzyl-2-(3-dimethylaminopropyl)benzimidazole starting from 2-(3-dimethylaminopropyl)benzimidazole and benzyl chloride, mp. 121°–122° C. (as fumarate).

EX. 6

1-(4-fluorobenzyl)-2-(3-dimethylaminopropyl)benzimidazole as an oil, starting from 2-(3-dimethylaminopropyl)benzimidazole and p-fluorobenzyl chloride.

Elementary analysis for $C_{19}H_{22}N_3F$

|  | C | H | N | F |
|---|---|---|---|---|
| calculated % | 73.28 | 7.12 | 13.49 | 6.10 |
| found % | 73.40 | 7.18 | 13.35 | 6.20 |

EX. 7

1-Tetrahydrofurfuryl-2-(3-dimeghylaminopropyl)benzimidazole as an oil, starting from 2-(3-dimethylaminopropyl)benzimidazole and tetrahydrofurfuryl bromide.

Elementary analysis for $C_{17}H_{25}N_3O$

|  | C | H | N |
|---|---|---|---|
| calculated % | 71.05 | 8.77 | 14.62 |
| found % | 70.88 | 8.90 | 14.58 |

EX. 8

1-(2-Ethoxyethyl)-2-(4-dimethylaminobutyl)benzimidazole as an oil, starting from 2-(4-dimethylaminobutyl)benzimidazole (mp. 104°–106° C.) and 2-ethoxyethyl chloride.

Elementary analysis for $C_{17}H_{27}N_3O$

|  | C | H | N |
|---|---|---|---|
| calculated % | 70.55 | 9.40 | 14.52 |
| found % | 70.12 | 9.32 | 14.61 |

EX. 9

1-(2-Ethoxyethyl)-2-(2-dimethylaminoethyl)benzimidazole starting from 2-(2-dimethylaminoethyl)benzimidazole (mp. 128°–130° C.) and 2-ethoxyethyl chloride.

analysis for $C_{15}H_{23}N_3O$

|  | C | H | N |
|---|---|---|---|
| calculated % | 68.93 | 8.87 | 16.08 |
| found % | 69.15 | 8.80 | 15.94 |

EX. 10

1-(2-Ethoxyethyl)-2-(3-diethylaminopropyl)benzimidazole as an oil, starting from 2-(3-diethylaminopropyl)benzimidazole and 2-ethoxyethyl chloride.

Elementary analysis for $C_{18}H_{29}N_3O$

|  | C | H | N |
|---|---|---|---|
| calculated % | 71.25 | 9.63 | 13.85 |
| found % | 71.40 | 9.60 | 13.91 |

EX. 11

1-(2-Ethoxyethyl)-2-(3-pyrrolidin-1-ylpropyl)benzimidazole as an oil, starting from 2-(3-pyrrolidinylpropyl)benzimidazole and 2-ethoxyethyl chloride.

Elementary analysis for $C_{18}H_{27}N_3O$

|  | C | H | N |
|---|---|---|---|
| calculated % | 71.72 | 9.03 | 13.94 |
| found % | 71.54 | 9.15 | 14.10 |

EX. 12

1-(2-Ethoxyethyl)-2-(3-diallylaminopropyl)benzimidazole starting from 2-(3-diallylaminopropyl)benzimidazole and 2-ethoxyethyl chloride.

Elementary analysis for $C_{20}H_{29}N_3O$

|  | C | H | N |
|---|---|---|---|
| calculated % | 73.36 | 8.93 | 12.83 |
| found % | 72.94 | 8.77 | 12.81 |

EX. 13

1-(2-Ethoxyethyl)-2-(1-methyl-2-dimethylaminoethyl)-benzimidazole, starting from 2-(1-methyl-2-dimethylaminoethyl)benzimidazole (mp. 168°–170° C.) and 2-ethoxyethyl chloride.

| Elementary analysis for $C_{16}H_{25}N_3O$ | | | |
|---|---|---|---|
| | C | H | N |
| calculated % | 69.78 | 9.15 | 15.26 |
| found % | 69.52 | 8.98 | 15.44 |

What we claim is:

1. A benzimidazole of the formula

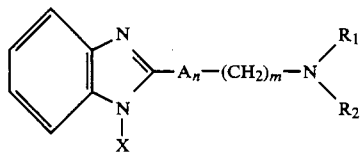

wherein

A represents

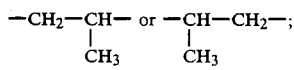

n is 0 or 1;

m represents 0 or an integer of from 1 to 5 inclusive, provided that when n is 0, m represents an integer of from 2 to 5 inclusive;

x represents a radical selected from the group consisting of fluorobenzyl, ethoxyethyl, allyloxy-ethyl and tetrahydrofurfuryl;

$R_1$ and $R_2$ each represent a saturated or unsaturated alkyl radical having from 1 to 4 carbon atoms or they may form, together with the adjacent nitrogen atom, an heterocyclc ring selected from the group consisting of pyrrolidine and piperidine.

2. 1-(2-Ethoxyethyl)-2-(3-dimethylaminopropyl)benzimidazole.

3. 1-Benzyl-2-(3-dimethylaminopropyl)benzimidazole.

4. 1-(4-Fluorobenzyl)-2-(3-dimethylaminopropyl)-benzimidazole.

5. 1-(2-Ethoxyethyl)-2-(2-dimethylaminoethyl)benzimidazole.

6. A pharmaceutical composition comprising an antihistamine effective amount of a compound according to claim 1 and a pharmaceutically acceptable carrier therefor.

* * * * *

UNITED STATES PATENT AND TRADEMARK OFFICE
CERTIFICATE OF CORRECTION

PATENT NO. : 4,971,980

DATED : November 20, 1990

INVENTOR(S) : GIANI et al

It is certified that error appears in the above-identified patent and that said Letters Patent is hereby corrected as shown below:

Column 5, line 58, "dimeghylaminopropyl" should read --dimethylaminopropyl--.

Column 6, line 22, before "analysis" insert --Elementary--.

Signed and Sealed this

Fourth Day of August, 1992

Attest:

DOUGLAS B. COMER

*Attesting Officer*      Acting Commissioner of Patents and Trademarks